United States Patent [19]

Triplett et al.

[11] 4,218,923

[45] Aug. 26, 1980

[54] SYSTEM FOR MONITORING THE CONDITION OF A PIPELINE

[75] Inventors: William C. Triplett, Ingleside; Walter H. Brauer, Houston; Robert Burke, Corpus Christi; Richard Morrow, Mission, all of Tex.

[73] Assignee: Triad & Associates, Inc., Robstown, Tex.

[21] Appl. No.: 10,032

[22] Filed: Feb. 7, 1979

Related U.S. Application Data

[63] Continuation-in-part of Ser. No. 866,486, Jan. 3, 1978, Pat. No. 4,162,635.

[51] Int. Cl.³ .......................................... G01N 29/04
[52] U.S. Cl. ..................................................... 73/623
[58] Field of Search ........................... 73/623, 622, 639

[56] References Cited

U.S. PATENT DOCUMENTS

| | | | |
|---|---|---|---|
| 2,995,925 | 8/1961 | Worlton | 73/623 X |
| 3,810,384 | 5/1974 | Evans | 73/623 X |
| 4,055,990 | 11/1977 | Topping | 73/623 |

Primary Examiner—James J. Gill
Attorney, Agent, or Firm—Kenway & Jenney

[57] ABSTRACT

Apparatus for scanning the interior of pipelines. The apparatus comprises a pig having an elongated body, a bogie assembly adapted to maintain the body in the center of a pipeline, and a seal assembly extending radially from the body and adapted so that the pig may be propelled by fluid flow through a pipeline. The pig further includes an on-board power supply coupled to the bogie assembly to provide and store electrical power for the pig. In addition, the pig includes an odometer, sensor and recording device powered by the power supply. The odometer is coupled to the bogie assembly and provides a motion signal representative of motion of the pig through a pipeline. The sensor includes a scanning ultrasonic surface wave exciter/transponder which generates a data signal representative of the interior condition of the pipeline. The recording device records the motion and data signals for subsequent analysis.

2 Claims, 10 Drawing Figures

SYSTEM FOR MONITORING THE CONDITION OF A PIPELINE

REFERENCE TO RELATED APPLICATION

This application is a continuation-in-part of U.S. Patent Application Ser. No. 866,486, "System For Monitoring The Condition Of A Pipeline", filed Jan. 3, 1978 now U.S. Pat. No. 4,162,635.

BACKGROUND OF THE INVENTION

The present invention relates to telemetry for detecting the condition of pipelines, and more particularly to pipeline scanners.

A major problem in the pipeline industry is the maintenance of existing pipelines and particularly the early detection of corrosion, leaks, delamination, and rupture. Left undetected, such conditions typically result in substantial losses due to impaired pipeline carrying capacity, contamination of the product, and actual loss of the product. In addition, such conditions are often accompanied by severe environmental consequences, property damage, and occasionally loss of life. Consideration of these factors has caused a substantial upsurge in the construction costs and cost of maintenance for pipelines, even to the point of delaying the building of vital energy-carrying lines.

The maintenance of a pipeline is best effected by the continuous monitoring of the pipeline condition, beginning immediately after installation and continuing to seepage leaks and major blowouts. Leaks or blowouts on land are relatively easy to discover, for example, by ground or air survey, with sufficient time to get repair crews to the site and contain any product spill and repair the line. However, underground and underwater pipelines are not readily monitored by such survey techniques. As a result, massive catastrophic blowouts may occur which may not be immediately detected, resulting in great damage to property and the environment. For example, a crude oil pipeline rupture may cause a spill which drifts for many miles before the leak is detected. Furthermore, the correction of such a rupture on an emergency basis requires extremely sophisticated and expensive seabottom mobile equipment, divers and support ships.

In order to aid in the maintenance of lines, there are many prior art devices which are adapted to internally scan pipelines by use of a so-called "pig" device which is periodically inserted through difficult-to-monitor stretches of the pipeline and transported under power of the fluid flow in the pipeline. The prior art pigs include sensors suitable for detecting certain classes of corrosion and leaks in the pipeline. However, the prior art system devices are generally extremely limited in many areas, for example, the precision and resolution of the fault detection. In addition, the method for logging the sensed parameters as the pig is transported through the pipeline provides relatively poor location capability for any detected faults. Furthermore, the prior art systems are generally provided with on-board battery systems for powering the sensing and data recording networks, resulting in a relatively large and bulky pig. For example, the prior art pigs may be on the order of two to three thousand pounds in weight and up to fortyeight inches in length.

In addition, the present pig insertion systems for pipelines include manual "lubricators" which require operator intervention to operate a lock configuration which injects a pig into the flow of a line.

Accordingly, it is an object of the present invention to provide a high resolution, high sensitivity pipeline condition monitoring device.

It is another object to provide a relatively compact and lightweight pipeline condition monitoring system.

It is still a further object to provide an automatic pig insertion means for use in conjunction with a pipeline to be monitored.

SUMMARY OF THE INVENTION

Briefly, a pipeline scanning apparatus, or pig, includes bogie and seal assemblies adapted to propel the pig along the product stream through a pipeline. The pig includes an on-board electrical power generator which is driven by the interaction of the assembly and the sidewalls of the pipeline and a high precision odometer and associated generator for providing a motion signal representative of movement through a pipeline. The pig further includes one or more sensors for generating data signals representative of physical characteristics of portions of the pipeline adjacent to the pig, and in addition, recording apparatus for recording both the motion signal and the physical characteristic data signals. Electrical power for the sensors and recorder is provided by the power generator. In one form of the invention, the sensors include a scanning ultrasonic surface wave exciter/transponder, a pressure transducer, and an inner diameter sensor.

The invention also comprises an automatic lubricator for inserting pigs into the pipeline at pre-programmed points in time. The lubricator, when activated in response to a pre-programmed signal, effectively closes off the main line and diverts fluid flow to an auxiliary line which includes the pig to be inserted. The diverted flow then powers the insertion of the pig into the main line. Following insertion, the main line is then reopened and the auxiliary line closed. In conjunction with this operation, an automatic pig inserter may be included to load a second pig into the auxiliary line. The second pig may be inserted into the main line at a later time in response to the next pre-programmed signal. As a result, a stretch of pipeline may be periodically monitored by pigs without operator intervention, other than to refill the stock of pigs for the automatic insertion.

At the end of the stretch of pipe, a conventional "runout" lubricator may be utilized to extract the pig. The pig may be then taken to a high speed analyzer, and its recording device fed to the analyzer to provide various visual and digital readouts plus preset alarm signals. In analysis of a pipeline section, the data from the pig may be compared with a prerecorded master tape of the same line area which is run concurrently, so that comparitive analysis may be made between the two sets of data.

As a result, a pipeline with an area in iminent danger of leaking, or rupturing, or one with a frank leak or rupture can be immediately diagnosed for subsequent replacement and repair. Since the odometer generated data distance base provides the exact location where the damage is located, a repair crew can provide an appropriate repair or close down the line in a minimum time.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
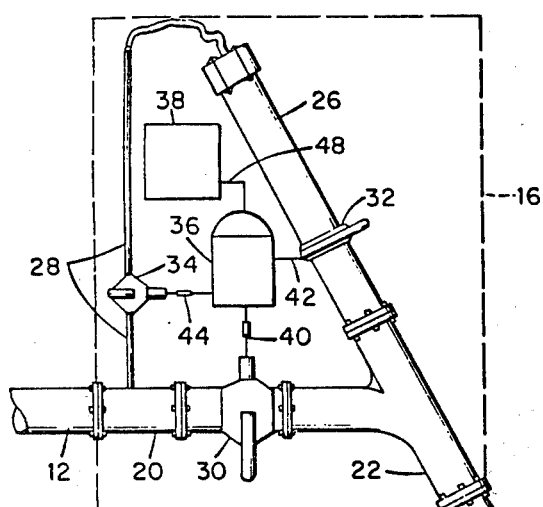
FIG. 1 shows a pipeline to be scanned and an apparatus for automatically inserting a scanning device in accordance with the present invention.

FIG. 1 shows a pipeline having a section-to-be-scanned 10, and upstream section 12 and downstream section 14. The sections 10 and 12 are coupled by way of an automatic lubricator 16 configured in accordance with the present invention, and the sections 10 and 14 are coupled by a convention "runout" lubricator 18. By way of example, the section-to-be-scanned 10 may be an underground or underwater portion of a liquid or gas pipeline comprising sections 10, 12 and 14.

Figure 2:
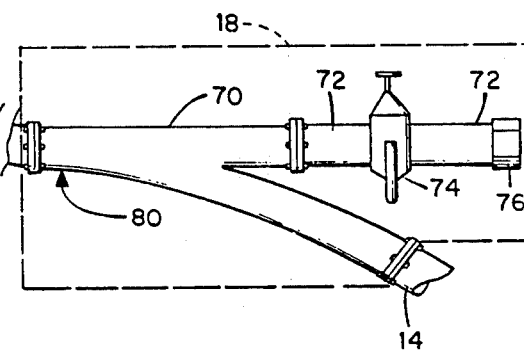
FIG. 2 shows in detailed form the device insertion apparatus of FIG. 1.
Figure 2:
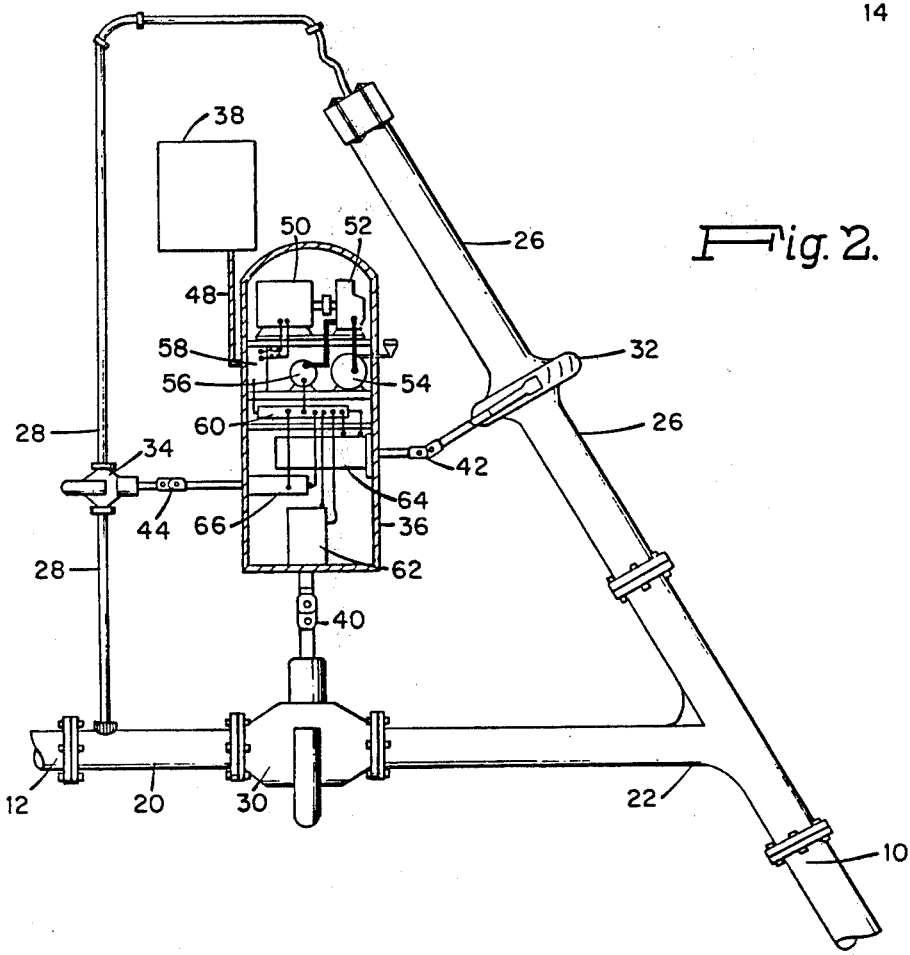

The lubricator 16 is shown in detailed form in FIG. 2. The lubricator 16 includes a main flow section 20 coupled to the upstream section 12, "Y" section 22, pig magazine section 26, and tap section 28 coupled between sections 20 and 26. The Y section 22 couples the magazine section 26 and main flow section 20 to the section 10. The lubricator 16 further includes hydraulic valves 30, 32 and 34 for controlling fluid flow through sections 20, 26 and 28, respectively. A hydraulic actuator 36 and associated controller 38 control the state of valves 30, 32 and 34 by way of linkages 40, 42 and 44, respectively. The hydraulic actuator 36 is responsive to the controller 38, which may be suitably programmed using conventional techniques to provide actuating signals to the hydraulic actuator 36 by way of line 48 whenever it is desired that a pig be inserted into the pipeline section-to-be-scanned 10.

As shown in FIG. 2, the hydraulic actuator 36 includes a pump motor 50 and associated hydraulic pump 52, fluid reservoir 54, and accumulator 56. A timing switch 58 is responsive to the control signals from controller 38 to actuate manifold 60 in a manner controlling hydraulic fluid flow to the hydraulic cylinders 62, 64 and 66, which in turn control the valves 30, 32 and 34, respectively, by way of the respective interconnecting linkages 40, 42 and 44.

In operation, a pig is inserted within the magazine section 26 at a point upstream of the valve 32. Prior to insertion of the pig, the valves 32 and 34 are closed and the valve 30 is open, thereby permitting fluid flow along the pipeline from upstream section 12 by way of sections 20, 22, 10 and 14. When a pig is to be inserted into the section 10, the controller 38 transmits an appropriate signal to the timing switch 58 which in turn controls manifold 60 to sequentially actuate cylinder 62 (closing valve 30), actuate cylinder 66 (opening valve 34), and actuate cylinder 64 (opening valve 32). In response, the main fluid flow from portion 12 is diverted by way of tap section 28 to the magazine section 26 and provides the force to displace the pig into the section 10. Following insertion of the pig, the timing switch 58 controls manifold 60 to sequentially close valve 34, close valve 32, and then open valve 30, thereby returning the pipeline flow path through sections 20 and 22. In alternative configurations, a pig loading assembly may be configured in conjunction with the magazine section 26 whereby pigs may be successively loaded into the magazine section 26 following each insertion through the portion 10.

The runout lubricator 18 is a conventional assembly which includes a "Y" section 70 coupling the section 10 with section 14 and a stub section 72. Lubricator 18 further includes a valve 74 and extraction cap 76. The section 70 includes a deflector on its interior surface at the point indicated by the arrow 80. The deflector is adapted to interact with a pig passing point 80, so that the pig is deflected to the stub section 72 rather than continuing on through the section 14. In order to extract the pig from the stub section 72, the valve 74 and extraction cap 76 may be opened.

Following removal of the pig, the valve 74 and cap 76 are closed. The data recording device from the pig may then be removed for processing by an external data processor using conventional techniques.

Figure 3:
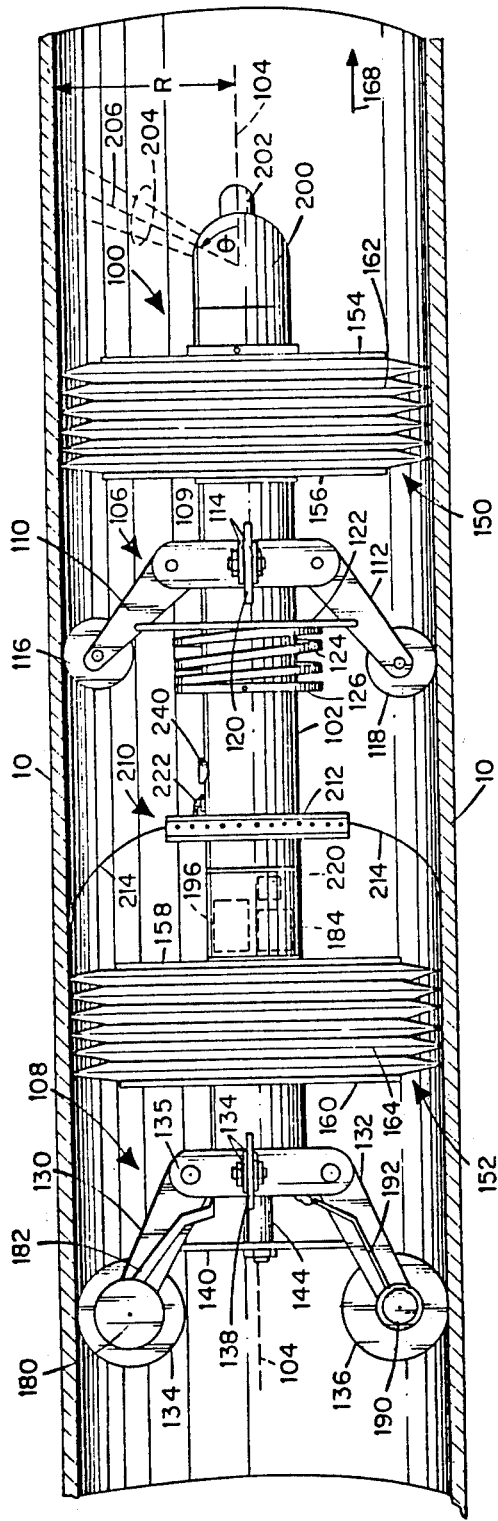
FIG. 3 shows an exemplary pipeline scanning device in accordance with the present invention.

FIG. 3 shows an exemplary pig 100 configured in accordance with the present invention and disposed within a pipeline section 10 (sectional view) having a nominal radius R. The pig 100 includes an elongated body member 102 having a longitudinal axis 104. Forward and aft bogie assemblies 106 and 108, respectively, are adapted to maintain the longitudinal axis 104 of the body member to be substantially coaxial with the central axis of the pipeline. The forward bogie assembly includes a yoke 109 which is affixed to the body member 102. Forward bogie arms 110, 112, 114 and 115 (not shown) are pivotally coupled at one end to the yoke 109 and at the other end to a respective one of bogie wheels 116, 118, 120 and 121 (not shown). The bogie arms are biased outwardly from axis 104 by a forward bogie plate 122, which is driven by a bogie spring 124 and a pressure plate stop 126 attached to the body member 102.

The aft bogie assembly 108 is similarly configured with arms 130, 132, 134 and 135 (not shown) being pivotally coupled at one end to a yoke 135 (attached to member 102), and at the other end to a respective one of bogie wheels 134, 136, 138 and 139 (not shown). The aft bogie arms 130, 132, 134 and 135 are biased outwardly from axis 104 by a pressue plate 140 and coupling shaft 144, which in turn is biased by a spring and stop plate assembly (not shown) internal to the body member 102. The aft bogie wheels include a non-skid tread on their peripheral surfaces to establish a frictional coupling with the interior surface of the pipeline section 10 so that those wheels rotate with respect to their associated arms as the pig moves through section 10.

The pig 100 further includes a two section sealing assembly, comprising forward seal 150 and aft seal 152. The seals 150 and 152 are affixed to the body 102 by retaining plates 154 and 156 (for the forward seal) and 158 and 160 (for the aft seal). Inflatable sealing members 162 and 164 are disposed between the plates for the seals 150 and 152 respectively. In alternative embodiments, different forms of sealing members (e.g. non-inflatable) may be utilized in keeping with the present invention.

The inflatable sealing members 162 and 164 extend radially outward from the body member 102. At their circumference, the members 162 and 164 are adapted so that a fluidtight seal is maintained between the members 162 and 164 and the inner surface of the pipeline section 10. As a result, the intermediate region between the seals 150 and 152 and interior to the pipeline section 10 is isolated from the region in front of the pig 100, and that intermediate region is also isolated from the region within the section 10 behind the pig 100. With this configuration, a pressure differential in the pipeline portion 10 between the region behind the pig 100 and the region in front of the pig 100 will cause motion of the pig from regions of relatively high pressure within the pipeline portion 10 to regions of relatively low pressure. The pig 100 is adapted to be inserted into the section 10 with the forward seal 150 adjacent to the relatively low pressure and the aft seal 152 adjacent to the relatively high pressure, e.g. so that pig 100 moves through section 10 in the direction indicated by arrow 168 at a velocity V related to the pressure differential existing across the pig.

In alternative forms of the invention, for example in a gas carrying pipeline, the seals 150 and 152 may be adapted to contain a liquid medium in the intermediate region which moves with the pig along the pipeline. This liquid medium may be especially adapted for use with various sensor assemblies carried by the pig, as described more fully below. In still other forms of the invention, a single section sealing assembly may be used.

An odometer assembly 180 is coupled to the wheel 134. Assembly 180 includes a generator which provides a signal representative of the rotation of wheel 134 with respect to the interior surface of section 10 of the pipeline. In alternative embodiments, a redundant odometer may be provided on the wheel 138 in order to eliminate possible error due to slippage of wheels 134 and 138. The signal produced by odometer 180 is referred to herein as the motion signal, and is representative of the motion of the pig 100 through the pipeline section 10. The motion signal is coupled by way of cable 182 to a signal recorder disposed within the body 102 and indicated generally by the block denoted 184 in FIG. 3.

An electrical power generator assembly 190 is coupled to the bogie wheel 136. The motion of the wheel 136 with respect to the inner surface of the portion 10 is transformed to electrical energy by assembly 190, which in turn is passed by way of cable 192 to an electrical energy storage means (indicated by block 196 within the body member 102), for subsequent use in powering the electrical components of the pig.

Pig 100 includes a plurality of sensor assemblies (powered by the electrical energy storage means 196) for detecting physical characteristics of portions of the pipeline section 10 adjacent to the pig as the pig moves through the pipeline.

The presently-described embodiment includes an ultrasonic surface wave exciter/transponder 200 mounted at the front end of the pig 100 between the body member 102 and a bumper assembly 202. The transponder 200 utilizes conventional techniques to excite ultrasonic surface waves in the pipeline, such as Rayleigh or Lamb waves, as described by D. Ensminger, *Ultrasonics—The Low and High Intensity Applications,* Marcel Dekker, Inc., New York 1973, and further to receive wave disturbances produced by the interactions of the surface waves with defects in the pipeline. The transponder 200 includes a transmitter for applying a narrow ultrasonic surface wave excitation beam to the pipeline interior surface, with the beam being at an acute angle $\theta$ with respect to the pig axis 104 (which is maintained coaxial with the axis of pipeline 10 by the bogie assemblies 106 and 108). The transducer 200 also includes a receiver for detecting oppositely directed defect-induced wave disturbances. The transmitted excitation beam (indicated by reference designation 204 in FIG. 3) is distributed about a central beam axis 206. The beam transmitter includes an adjustable collimating device for establishing a beamwidth L in the direction of the pipeline axis at a distance R from that axis, and a beamwidth $\Delta$ in the direction as transverse to its central axis at a distance R from that axis, where $\Delta$ is small compared with the circumference of the inner surface of the pipeline section 10. The transponder 200 also includes a conventional means for adjustably rotating the transmitter and receiver at a selected angular velocity equal to $2\pi$ V/L radians per second. With this configuration, as the pig 100 moves through the pipeline section 10, the excitation beam is scanned circumferentially along the inner pipe surface on a helical path so that the entire interior surface of the pipeline section 10 is covered.

The present embodiment is suitable for use in a liquid-carrying pipeline where the ultrasonic surface wave excitation beam is emitted into the liquid flowing within the pipeline. In alternative embodiments, the transponder 200 may be configured in the intermediate region between the seals 150 and 152 which may include a liquid medium different from the either gas or liquid product carried by the pipeline. For example, a high density silicone liquid may be utilized in the monitoring of gas-carrying or empty pipelines.

The transponder 200 also includes a transducer for generating sensor data signals representative of the received defect-induced wave disturbances. In some embodiments, data representative of the receiver angle may be generated in conjunction with this sensor data.

In operation, the beamwidth of the ultrasonic surface wave excitation beam is adjusted to match the planned rate of travel of the pig through the pipeline section 10 so that the entire interior surface may be scanned. In some embodiments, the transmitted excitation beam angle $\theta$ is adjusted to be a suitable acute angle to minimize the depth of penetration of the resultant surface wave and with a calculated forward angularity to match the proposed rate of travel in the pig. Thus, the surface wave is directed to travel circumferentially on and just under the inner pipe surface. As the incident beam travels around the interior of the pipeline section 10, discontinuities from defects cause reflections in the surface wave. The reflected surface wave causes a wave disturbance in the region within pipeline section 10 which travels in a relatively broad front back to the sensor in the transponder 200. This sensor in turn provides a time of return recording data signal which is transferred to a data multiplexer (indicated generally by reference numeral 220 in FIG. 3) and then to the data recorder 184 for recording in a predetermined time relationship with the motion signals produced by the odometer assembly 180. In the present embodiment, the ultrasonic surface wave excitation beam is generated in pulse form so that the return pulses may be identified in terms of transit time. A particular advantage of the pulsed emission is the reduction in power requirement.

In the present embodiment, the pulse repetition frequency is approximately 100 kilohertz with wave length approximately 1–5 millimeters (which may be adjusted to vary the resolution of the defect-caused reflections in order to optimize the detection characteristics for a particular application). With the present configuration, variations in pipeline wall thickness may be measured to a sensitivity of less than 0.005 inches, and such variations may be located to within a few feet. In addition, see page or frank ruptures may also be located within a few feet.

Accordingly, the transponder 200 operates as a high resolution ultrasonic radar that provides data signals representative of pipeline interior surface irregularities, such as cracks, scaling, weakened areas caused by corrosion, terrain shifting, and the like. By adjusting the wave length of the induced surface waves, the resolution can also be adjusted to locate hairline cracks and other small flaws which may subsequently grow to relatively large and costly breakage if left unrepaired.

Figure 5:
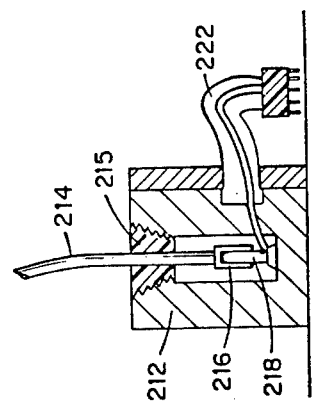
FIGS. 4 and 5 show in detailed form the inner diameter sensor of the scanning device of FIG. 3.

The present embodiment also includes an inner diameter (ID) sensor 210 for generating data signals representative of the inner diameter of portions of the pipeline section 10 adjacent to the pig 100. The sensor 210 is shown in detailed form in FIGS. 4 and 5. The sensor 210 includes a yoke assembly 212 affixed to and extending about the circumference of body member 102. A plurality of uniform length, elongated, resilient whisker members 214 extend radially with respect to the axis 104. By way of example, the whisker members may be made from spring steel. The whisker members 214 are of sufficient length to interferingly engage with the inner surface of the pipeline section 10 at their distal ends. The other ends of whisker members 214 are each coupled to the yoke 212 through an elastic plug 215. Each of whisker members 214 includes an exciter yoke 216 which is mechanically coupled to a piezoelectric transducer 218. Each transducer 218 is electrically coupled to a data multiplexer 220 by way of a cable 222. In operation, the whisker members 214 interferingly engage with the interior portion of pipeline section 10. Variations in that surface (such as due to corrosion or pitting) are transformed to electrical signals by the crystal 218. The data generator 220 provides data signals representative of these variations to the data recorder 184.

Figure 6:
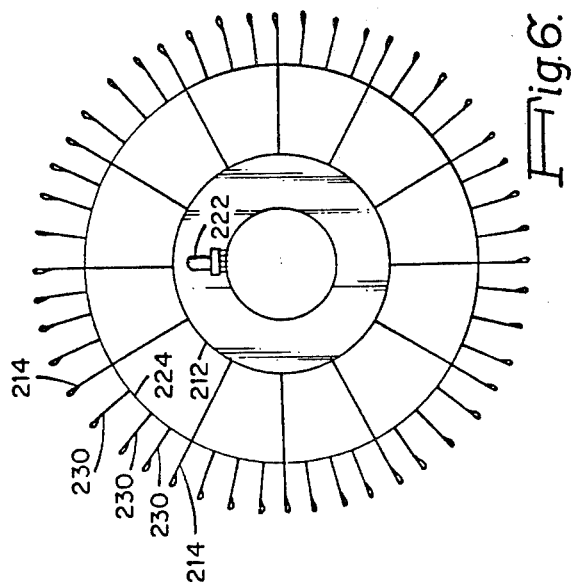
FIG. 6 shows in detailed form an alternative embodiment of the sensor of FIGS. 5 and 6.
Figure 4:
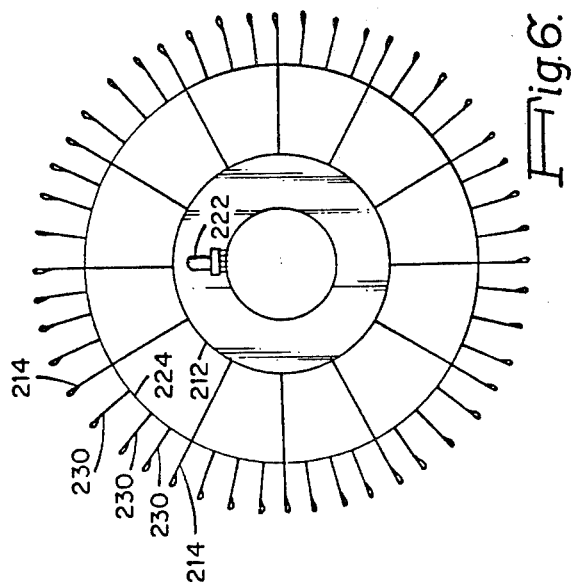

FIG. 6 illustrates an alternative form for the ID sensor assembly shown in the FIGS. 3 and 4 embodiment. This form is suitable for use in relatively large diameter pipelines, and includes a series of coupling members 224 which interconnect the adjacent ones of the whisker members 214. The coupling members 224 include a plurality of elongated, resilient secondary whisker members 230 extending radially outward with respect to axis 104 from the yoke 212. The length of the secondary whiskers is selected so that the tips of the secondary whiskers 230 are the same distance from the axis 104 as the tips of the primary whiskers 214.

Figure 7:
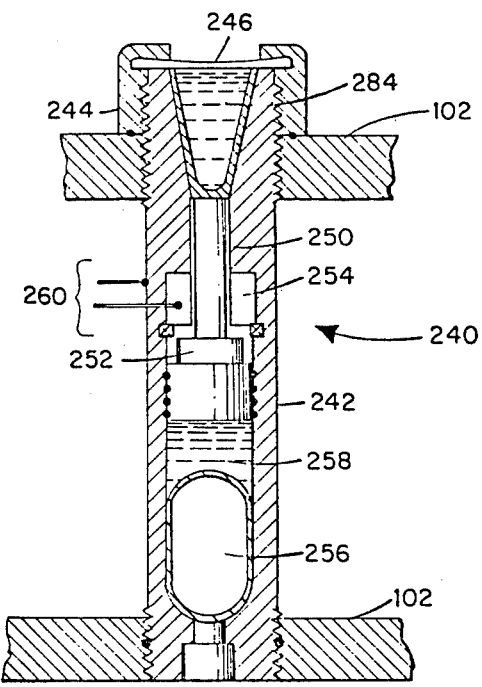
FIG. 7 shows in sectional view the pressure sensor of the scanning device of FIG. 3.

The pig 100 further includes a high sensitivity pressure transducer 240, shown in detailed form in FIG. 7, for producing a data signal representative of pressure variations within the intermediate region between seals 150 and 152 interior to the pipeline section 10.

The pressure sensor 240 includes a housing 242 which is rigidly coupled across the diameter of the body member 102. The housing 242 includes a cap 244 for maintaining a pressure sensitive diaphragm 246 in contact with the intermediate region. The diaphragm 246 is coupled against a fluid reservoir 284 so that variations in position of the diaphragm 246 are transformed to pressure waves within the reservoir 284, which in turn drive a piston rod 250 against a pressure plate 252. The pressure plate 252 is biased against a piezoelectric crystal 254 by a high pressure air reservoir 256 coupled by a fluid reservoir 258.

In operation, the air pressure reservoir 256 biases the pressure plate 252 against the crystal 254. In response to variations in pressure sensed by the diaphragm 256, the biased pressure on crystal 254 is varied. These variations are transformed by crystal 254 to an electrical signal which is coupled by way of cable 260 to the data recorder 184.

The data recorder 184 is a conventional tape cassette machine powered by the power supply 196. The data multiplexer 220 receives the motion and sensor data signals from the odometer 180, the Lamb wave transponder 200, the inner diameter sensor 210 and pressure sensor 240 and provides a multiplexed signal suitable for recording on the tape cassettes of recorder 184 using conventional data multiplexing techniques.

Figure 8A:
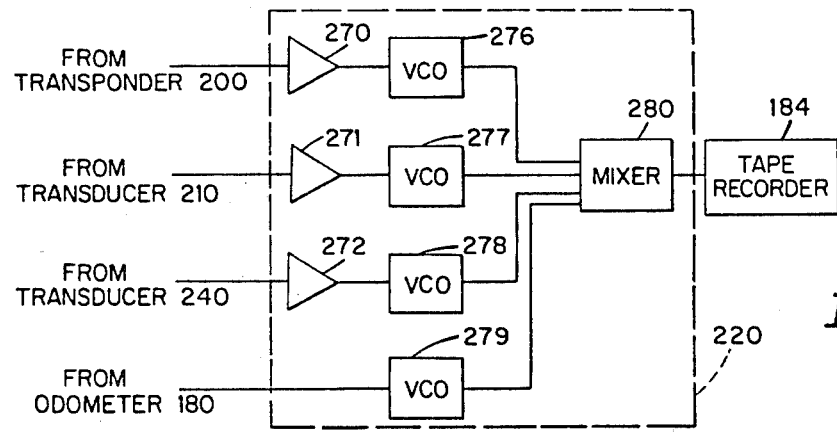
FIG. 8A shows in block diagram form the exemplary data recorder and multiplexer for the embodiment of FIGS. 1–7.
Figure 8B:
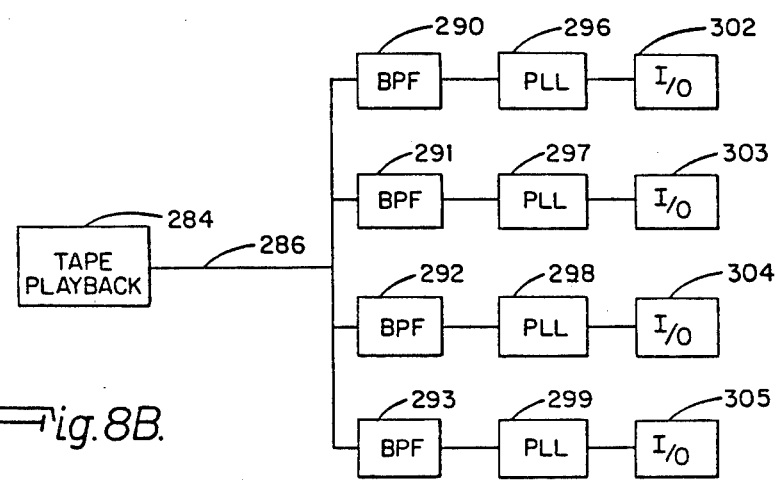
FIG. 8B shows in block diagram form an exemplary data retrieval system for the embodiment of FIGS. 1–7.

By way of example, FIG. 8A shows an exemplary data recorder 184 and multiplexer 220 suitable for use with the present invention, and FIG. 8B shows an exemplary data extraction system in which the tapes may be played back and the various sensor data extracted for subsequent analysis.

As shown in FIG. 8A, the multiplexer 220 includes d.c. amplifiers 270–272, respectively coupled to transponder 200, transducer 210 and transducer 240. These amplifiers amplify the relatively weak signals generated by the various sensors and increase the signals to appropriate levels for driving voltage controlled oscillators 276–278, respectively. The output from odometer 180 keys voltage controlled oscillator 279 to be on or off, thereby generating a pulse for every complete rotation of the wheel 134. This oscillator can also be frequency shift keyed (FSK) to indicate passage of an interval of time, thereby providing distance and time measurements in a single stage. The outputs from voltage controlled oscillators 276–1279 are applied to a mixer network 280. The resultant signal is applied to a conventional cassette tape recorder 184.

The exemplary data retrieval system of FIG. 8B includes a tape playback device 284 which couples the recorded data through an audio bus 286 to a series of tunable audio bandpass filters (BPF's) 290–293 and associated phase lock loops (PLL's) 296–299 and input/output (I/O) devices 302–305. Each phase lock loop is tuned to the telemetry tone associated with its coupled filter and the related VCO in unit 220. The I/O devices may comprise a strip recorder, or other device, for recording the data in a form suitable for subsequent analysis. The BPF-PLL combinations are adjustable in frequency to accommodate variations in recorder speeds so that by recording a calibration section for the start of each run, the filters and associated PLL can be calibrated to that individual set of tones, thereby permitting difference in recorder and playback speeds to be compensated.

With the present invention, a high resolution and high sensitivity pipeline condition monitoring device may be provided. For example, the present embodiment may be readily configured to be 2½ inches in diameter, 24 inches in length and approximately 20 pounds in weight. With this configuration, suitable seals may be employed for use in monitoring pipes ranging from 4 inches up to 48 inches in diameter, or more. Furthermore, the automatic lubricator permits the periodic scanning of pipeline sections without operator intervention.

Figure 9:
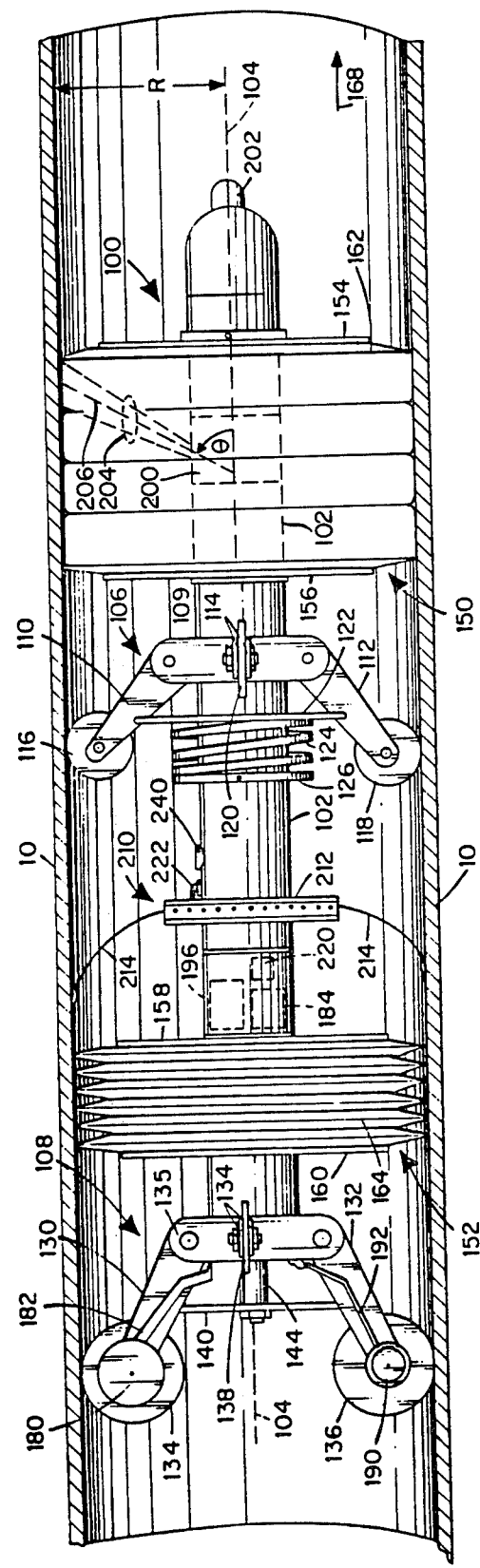
FIG. 9 shows another exemplary pipeline scanning device in accordance with the present invention.

FIG. 9 shows an alternative embodiment of the present invention, which is generally similar to the embodiment of FIG. 3. In FIG. 9, elements corresponding to elements in the embodiment of FIG. 3 are denoted with identical reference numerals.

In the FIG. 9 embodiment, the pig 100 includes the two section sealing assembly comprising forward seal 150 and aft seal 152. The seal 150 includes pressure plates 154 and 156 and a fluid-filled flexible membrane 162. In that assembly, plate 154 is movable along the body 102 while the plate 156 is affixed to the body 102. Similarly, the aft seal 152 includes pressure plates 158 and 160 and a fluid-filled, flexible membrane 164. For this latter seal, the plate 160 is movable along the body 102 while the plate 158 is affixed to body 102. In the present embodiment, the inflatable sealing members 162 and 164 define a generally toroidal region between the body member 102 and the inner surface of a portion of pipeline section 10. This toroidal region is filled with a liquid phase medium which extends the members 162 and 164 radially outward from the body member 102 so that at their outermost edges, the members 162 and 164 provide fluid-tight seals between the members 162 and 164 and the respective portions of the inner surface of the pipeline section 10. As the pig 100 moves through the pipeline in the direction 168 in response to fluid pressure in the pipeline, the pressure plate 160 is pressed toward the fixed plate 158 to maintain the membrane 164 against the pipeline inner surface. As the pig 100 moves through the fluid in the pipeline, the movable pressure plate 154 is pressed toward the fixed plate 156 to maintain the membrane 162 against the pipeline inner surface.

In the embodiment of FIG. 9, the transponder 200 (shown by dashed lines) is positioned in body 102 at a point within the forward seal 150. The transponder 200 is substantially similar to the transponder 200 as described in conjunction with the embodiment of FIG. 3, except that the excitation beam from the transponder to the pipeline interior surface is substantially within the forward seal 150. With this configuration, the fluid medium within the seal acts as a coupling medium for the excitation beam and response wave disturbance. At the edge of the membrane-to-pipeline interface, the excitation beam is coupled to the pipeline inner surface to establish ultrasonic surface waves. The transponder 200 also includes a transducer for generating sensor data signals representative of received defect-induced wave disturbances from the inner surface of the pipeline. In alternative embodiments, the transponder 200 may be positioned within the aft seal 152. In still other embodiments, there may be one or more additional flexible membrane couplers along the length of pig 100, any one of which may include the ultrasonic wave transducer 200.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. Apparatus for scanning the interior of a pipeline having a radius R, comprising:
   A. an elongated body member having a longitudinal axis, having a power supply disposed therein,
   B. bogie assembly including means for maintaining the longitudinal axis of said body member substantially coaxial with the central axis of said pipeline,
   C. sealing means extending radially from said body member, and including means for establishing a fluid-tight seal between regions in a pipeline ahead of said apparatus and regions behind said apparatus, whereby said apparatus is responsive to the pressure differential across said sealing means to move at a velocity V along said pipeline axis from regions of relatively high pressure to regions of relatively low pressure,
   D. sensor means powered by said power supply for detecting one or more physical characteristics of portions of said pipeline adjacent to said apparatus, and for generating sensor data signals representative of said conditions, said sensor means including:
   coupling means including a flexible membrane for containing a liquid phase medium in a toroidal region between said body member and a portion of the interior surface of said pipeline adjacent to said apparatus, and
   an ultrasonic surface wave transponder including:
   i. means for transmitting an ultrasonic surface wave excitation beam within said toroidal region of said coupling means at an angle $\theta$ with respect to said pipeline axis, where $\theta$ is measured from said pipeline axis ahead of said body member and is less than $\pi/2$ radians, and for receiving an oppositely directed wave disturbance, said transmitted beam being adapted to pass through said toroidal region and said flexible membrane and excite ultrasonic waves on the interior surface of said pipeline, and having a beam width at least equal to L in the direction of said pipeline axis at a distance R from said axis, and a beam width $\Delta$ which is small compared with $2\pi R$ in the direction transverse to said axis at a distance R from said axis,
   ii. means for rotating said transmitting and receiving means at an angular velocity equal to $2\pi V/L$ radians per second, and
   iii. means for generating an ultrasonic surface wave sensor data signal representative of said received wave disturbance, said surface wave sensor data signal being representative of the interior surface condition of said pipeline at the point of incidence on said pipeline of said transmitted excitation beam.

2. Apparatus according to claim 1 wherein said excitation beam transmitting means is adapted to transmit a pulsed beam.

* * * * *